United States Patent
Thal

[19]

[11] Patent Number: 6,045,574
[45] Date of Patent: Apr. 4, 2000

[54] SLEEVE AND LOOP KNOTLESS SUTURE ANCHOR ASSEMBLY

[76] Inventor: Raymond Thal, 11321 Bright Pond La., Reston, Va. 22094

[21] Appl. No.: 09/283,217

[22] Filed: Apr. 1, 1999

[51] Int. Cl.[7] .............................. A61B 17/04; A61F 17/58
[52] U.S. Cl. .............................................. 606/232; 606/73
[58] Field of Search ................................ 606/232, 72–75, 606/224

[56] References Cited

U.S. PATENT DOCUMENTS

| | | |
|---|---|---|
| 4,007,743 | 2/1977 | Blake . |
| 4,532,926 | 8/1985 | O'Holla . |
| 4,632,101 | 12/1986 | Freedland . |
| 4,721,103 | 1/1988 | Freedland . |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. . |
| 5,141,520 | 8/1992 | Goble et al. . |
| 5,192,303 | 3/1993 | Gatturna et al. . |
| 5,207,679 | 5/1993 | Li . |
| 5,224,946 | 7/1993 | Hayhurst et al. . |
| 5,236,445 | 8/1993 | Hayhurst et al. . |
| 5,370,662 | 12/1994 | Stone et al. . |
| 5,569,306 | 10/1996 | Thal . |
| 5,658,313 | 8/1997 | Thal . |
| 5,662,654 | 9/1997 | Thompson .............................. 606/232 |
| 5,665,112 | 9/1997 | Thal . |
| 5,683,419 | 11/1997 | Thal . |
| 5,709,708 | 1/1998 | Thal . |
| 5,720,765 | 2/1998 | Thal . |
| 5,728,136 | 3/1998 | Thal . |

*Primary Examiner*—Michael Buiz
*Attorney, Agent, or Firm*—Hoffman, Wasson & Gitler

[57] ABSTRACT

A sleeve and loop knotless suture anchor assembly for attachment of tissue to bone mass. The assembly includes a hollow anchoring sleeve with a suture loop attached thereto and an anchor device for capturing the loop with a snag element or recess thereon or therein the anchor device. Once the loop is captured, the anchor is inserted securely into the hollow anchoring sleeve which is installed in the bone mass which facilitates a repair of the torn away soft tissue.

8 Claims, 5 Drawing Sheets

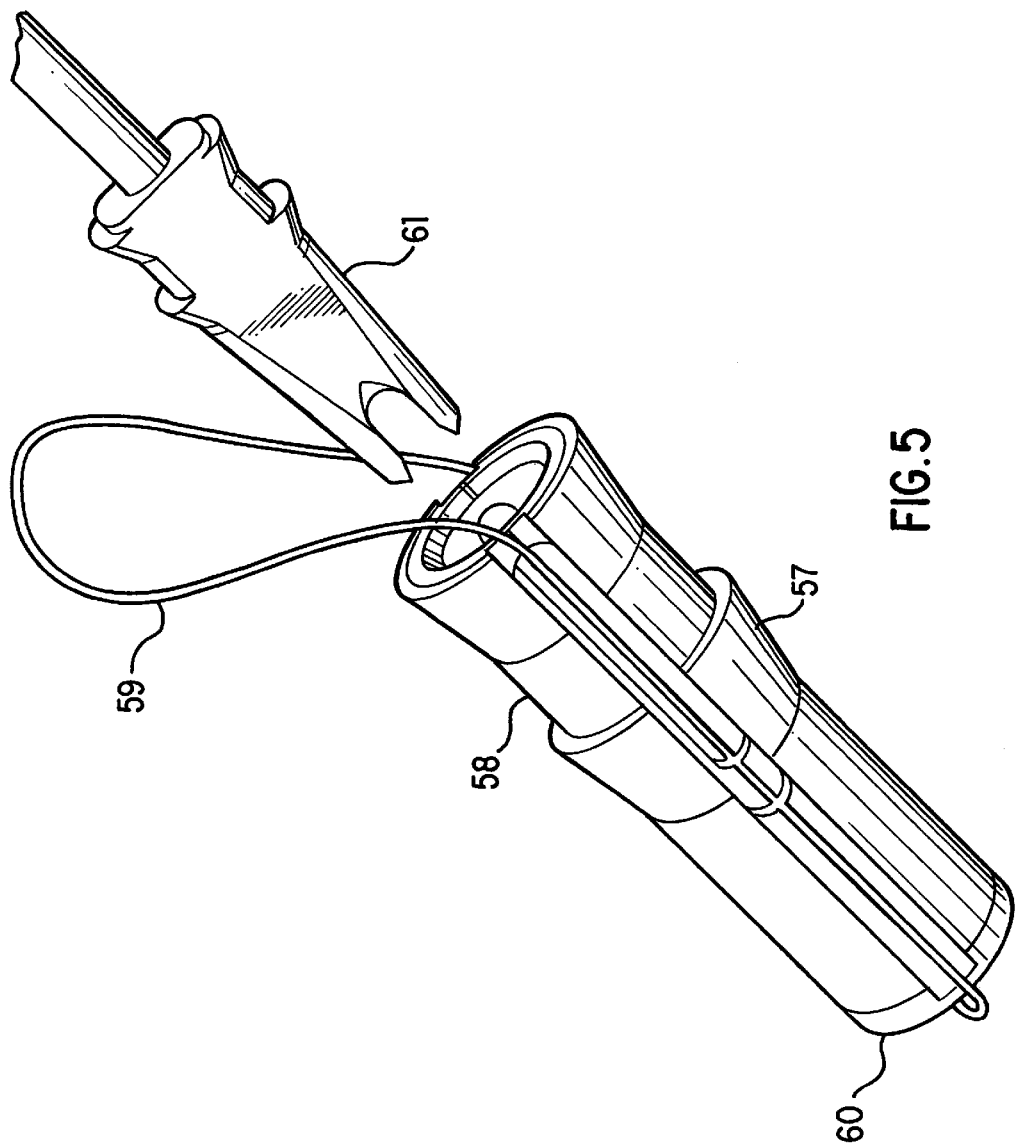

SLEEVE AND LOOP KNOTLESS SUTURE ANCHOR ASSEMBLY

BACKGROUND OF THE INVENTION

1. Field of the Invention

The present invention relates to a process and device or assembly for use in tissue repair. More particularly, there is provided an enhanced assembly that enables the attachment together or repair of portions of biological tissue, such as tendons or ligaments, to a bone surface. Such device or assembly is used in an unique way with novel components to reattach or attach tissue to bone.

2. Description of the Background Art

Soft tissues, such as tendons and ligaments, generally are attached to bone by small collageaous fibers. These connections are strong but permit the tendons and ligaments to be flexible. When a tissue, or a portion of a tissue, is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunneling techniques. These attachment devices are usually inserted through extensive surgical incisions and, in some circumstances, by arthroscopic surgical techniques. The pulse of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique free loop knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as prostheses, to bone. A suture anchor assembly is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

The applicant has developed a number of mechanisms for a tissue to bone repair which are disclosed in U.S. Pat. Nos. 5,569,306; 5,683,419; 5,728,136; 5,665,112; 5,658,313; 5,720,765; and 5,709,708.

It is an object of the present invention to provide a knotless suture anchor assembly which is easy to use and install.

Another object of the present invention is to provide a loop and sleeve suture anchor assembly which allows for secure attachment of soft tissue to a bone mass without the use or requirement of tying a knot during the surgical procedure.

Still another object of the present invention is to provide a suture anchor assembly which is compact and allows a surgeon to easily guide the anchor means into a sleeve in the bone mass, to enhance the security of the repair.

Yet another object of the present invention is to provide a process whereby a plurality of loop and sleeve knotless suture anchor assemblies can be used to effectively attach or reattach tissue to bone.

Further, another object of the present invention is a mechanism for producing incisions or cuts in tissue for performing reattachment or attachment of tissue to bone using the novel anchor assemblies.

A primary feature of the present invention is to provide loop and sleeve knotless anchor assembly that includes an unique snag-type or capture means on an anchoring means which facilitates engagement of the anchor means with to a continuous suture loop which has been attached to a hollow anchoring sleeve, for drawing soft tissue to the bone mass.

SUMMARY OF THE INVENTION

In accordance with the above objects, the present invention is directed to an assembly and a process of using at least one knotless suture anchor assembly for attachment or reattachment of biological soft tissue to bone. The unique enhanced loop and sleeve knotless suture anchor assembly may include one or a plurality of anchor means which can either be installed into a hollow anchoring sleeve which has been installed into a bone mass. The hollow anchoring sleeve or anchor means can have varying shaped or surfaced exteriors for secure capturing or engagement with a bone mash. Each anchor means engages a suture loop which has been at-ached to the hollow anchoring sleeve and also has been passed through the tissue.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying structures which may embody the anchor means or the exterior of the anchoring sleeve of the invention.

Further, if desired, the hollow anchoring sleeve can contain a collar on the rear section or recur side to control the depth of sleeve insertion into the bone and prevent excessive insertion depth. The anchor means of the assembly has a first end or configuration which allows for secure capturing of the hollow anchoring sleeve and a snag component for securing the loop suture element which is attached to the hollow anchoring sleeve. The first end of the anchor can be pointed or frustoconical in shape. The anchor means can be ribbed, beaded, threaded, or expandable on its exterior surface or further can contain one or more prongs for secure mating with the anchoring sleeve.

The anchor means has located thereon or therein unique snag means in the shape of a hook, or other type projection, or a recess cut into the anchor means, or a slit cut into an existing opening in the anchor, for engaging the continuous loop of a suture element which is attached to the hollow anchoring sleeve. One particular embodiment provides a recess at the apex of the anchor whereby the loop suture element is snagged or captured by the anchor.

The loop suture element can be a single continuous loop configuration or a plurality of suture lengths tied or attached to form a loop by any suitable means. The suture element is attached to the top of the hollow anchoring sleeve by any desired mechanism. A hook portion or projection of the anchor means can be made of the same material as the entire anchor means or a different material, as desired. The anchor assembly can be inserted during an open procedure, or an endoscopic procedure. In a preferred method, a first portion of the loop suture element is passed through the soft tissue. Next, the hollow anchoring sleeve is installed into the bone mass by any suitable mechanism or means. In another preferred method, this procedure can be reversed with the sleeve being installed into the bone mass prior to the suture being pulled. The suture loop is then captured by the snag means of the anchor. The anchor means is then inserted into a hollowing anchoring sleeve which has been inserted into the bone mass.

If desired, an user can use a plurality of assemblies to effectuate a broader repair.

The incisions, cuts or passages in the tissue can be accomplished by using needle and suture loop attachment assemblies which have been added to the loop suture element. Upon capture of the loop suture element the needle and suture loop attachment assembly is cut away and discarded. This assembly facilitates the method of stitching and reattachment.

Numerous other features of various embodiments of the enhanced sleeve and loop knotless suture anchor assembly will be apparent from the following detailed description and the accompanying drawings.

BRIEF DESCRIPTION OF THE DRAWINGS

FIG. 5 is a depiction of an alternate embodiment of a hollow anchoring means with suture loop;

DETAILED DESCRIPTION OF THE PRESENT INVENTION

Figure 1:
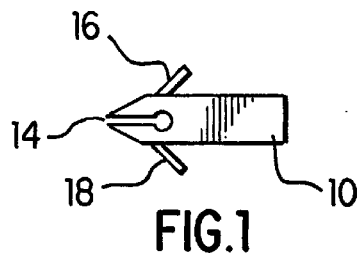
FIG. 1 is a perspective view of an anchor means having a depression or snag recess.
Figure 2:
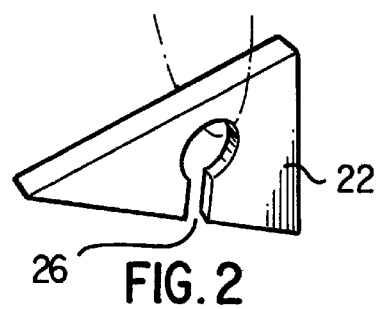
FIG. 2 is a perspective view of a wedge-type anchor means having a recess snag means.
Figure 3:
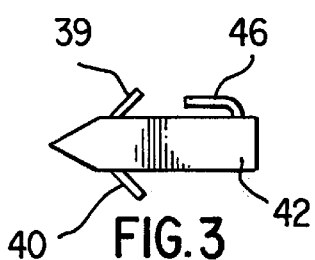
FIG. 3 is an alternate embodiment of an anchor means having a snag element.

Referring to FIGS. 1, 2 and 3, there is depicted three embodiments of anchor means containing snag recesses or snag means for capturing a free loop suture element. More particularly, FIG. 1 illustrates an anchor means 10 having prongs 16 and 18 which facilitate the attachment of the anchor means 10 to a bone mass. Provided in the body of the anchor means is a snag recess 14 for capturing a free loop suture element. The device can also contain, or be configured, with umbrella spokes or any other type of engaging features on its exterior for securing an attachment with a bone mass. All of these exterior attachment features are known to the industry and incorporated herein by reference.

FIG. 2 illustrates an alternate embodiment of the anchor means. Depicted is a wedge-like anchor means 22, and a snag means 26.

FIG. 3 illustrates another alternate embodiment of the present invention. Depicted is an anchor means 42, a snag means 46 located at a rear portion of the anchor means 42. Also pictured in this embodiment are two prongs 39 and 40 for secure attachment or mating with a bone mass or a hollow anchor assembly.

Figure 4:
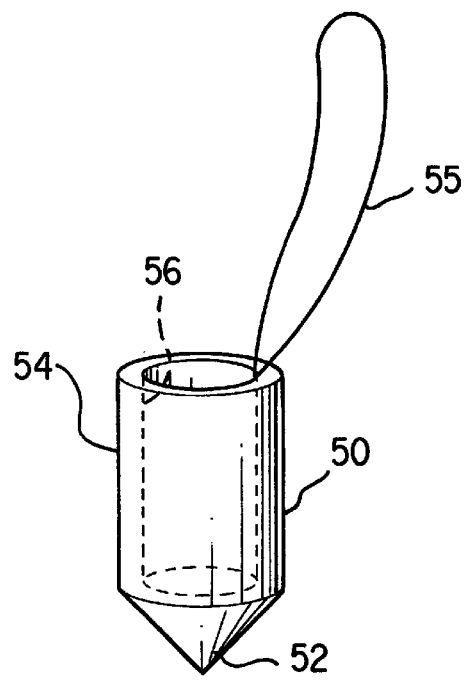
FIG. 4 is a depiction of a hollow anchoring means with suture loop.
Figure 6:
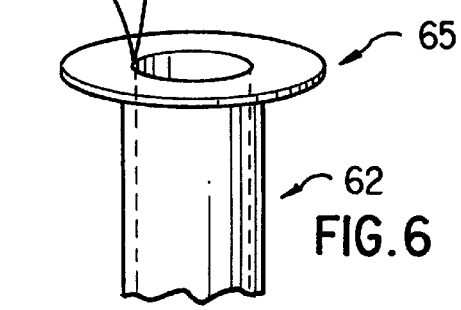
FIG. 6 is a depiction of an alternate embodiment of an anchoring means having a collar and a suture loop.

FIGS. 4–6 depict three potential structures for a hollow anchoring means which can be utilized in conjunction with an anchor means for the desired repair. FIG. 4 depicts a hollow anchoring means 50 which has a pointed end for penetration into a bone mass. The exterior of the hollow anchoring means 54 may be smooth, or may contain a rough exterior for gripping a bone mass. The exterior can have prongs, ribs, threads, or any suitable means for securely gripping the bone mass. In addition, any type of secure attachment means may be placed on the exterior 54 of the hollow anchoring means 50 for a secure attachment. Likewise, on the interior surface 56 such may be smooth or may be roughed or may contain any type of material or surfacing or means for securing gripping of an anchor means which is placed therein. Attached in any manner desired is a suture loop 55 to the hollow anchoring means 50. The suture loop 55 may be one continuous loop or a plurality of sutures tied to form a loop.

FIG. 5 depicts an embodiment of a hollow anchoring means 58. The hollow anchoring means 58 has a flat or rounded bottom end 60 and can be used for desired procedures. The embodiment includes a suture loop 59. This loop can be continuous or a plurality of tied loops forming ore loop. Also depicted is an anchor 61 which will mate with the hollow anchoring means 58. As is stated above, the exterior and interiors of the sleeve can be the same as that of the first embodiment. This particular structure has an expandable exterior surface 57.

Further, in FIG. 6 there is depicted an alternate embodiment of the top portion of a hollow anchor means 62. The top portion of any embodiment of the hollow anchoring means may contain a lip 65 which grips the surface of a bone mass once the hollow anchoring means is placed into a pre-drilled hole in a bone mass. This embodiment also contains a suture loop 63 as described above.

Figure 7:
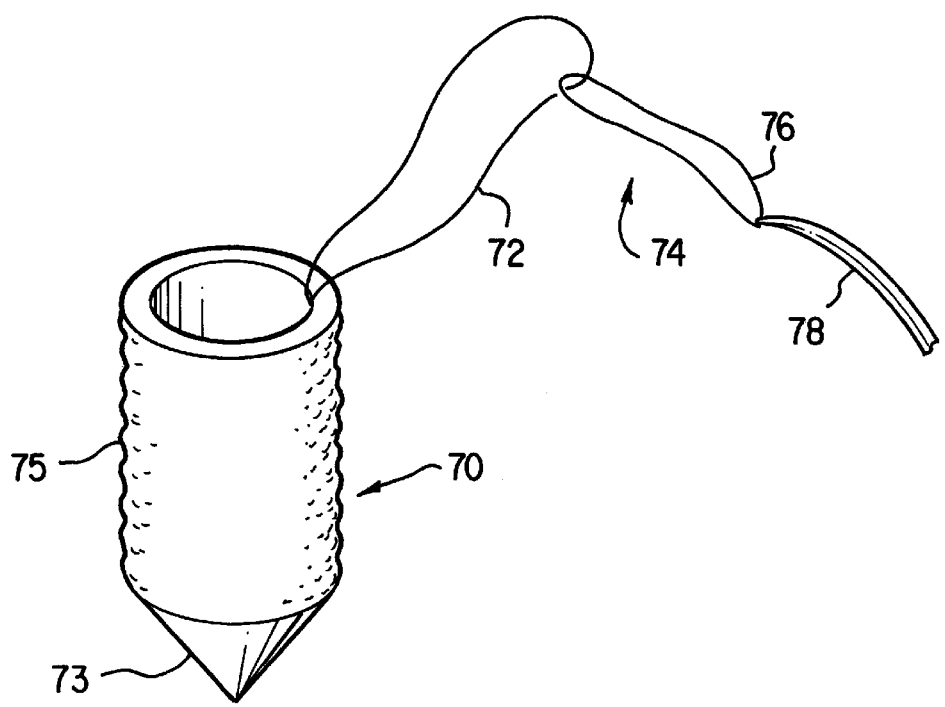
FIG. 7 is a depiction of a loop and sleeve anchoring device having a suture piercing means.
Figure 8:
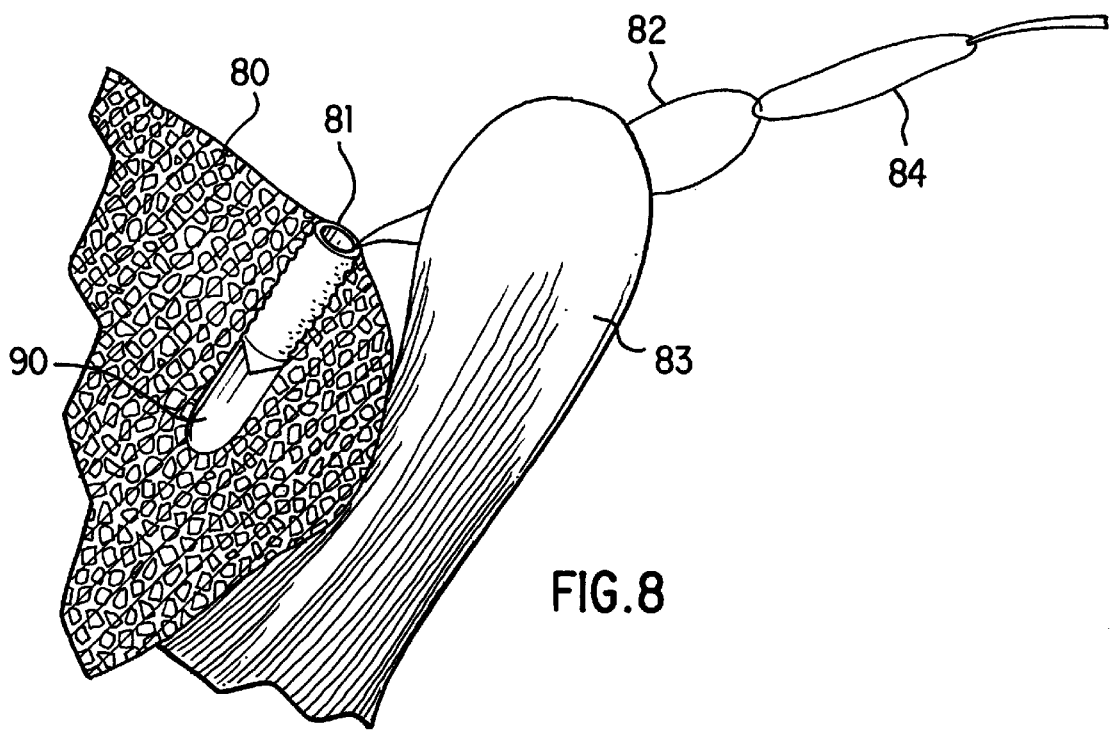
FIGS. 8–11 are a step by step depiction of a process of performing a tissue repair using the loop and sleeve knotless anchor assembly of the present invention.

FIG. 7 illustrates a hollow anchoring sleeve 70 as depicted in FIG. 4. Provided along with the suture loop element 72 is a needle suture breakaway element 74. The breakaway element is comprised of a suture loop 76, and a needle 78. The breakaway element is used to pierce tissue and draw the suture loop element 72 there through during the attachment or reattachment procedure. Also depicted in this embodiment is a roughened surface 75 of the sleeve to facilitate gripping of a bone mass, and a pointed edge 73 for penetration of the bone mass.

FIGS. 8, 9, 10 and 11 depict a method for reattaching or attaching tissue to bone using an embodiment of the invention.

In FIGS. 8–11, there is depicted a bone mass 80 and a tissue element 83. Also illustrated is a pre-drilled hole 90 and a suture loop element 82 which is attached to the hollow anchoring sleeve 81 and will facilitate the repair. Also depicted is a needle suture breakaway element 84 which is utilized during a repair procedure. Breakaway element 84 is pulled through tissue 83 in a first step of the repair. Alternately, hollow anchoring sleeve 81 can be first inserted into bone mass 80 prior to the pulling through of the needle suture breakaway element.

Figure 9:
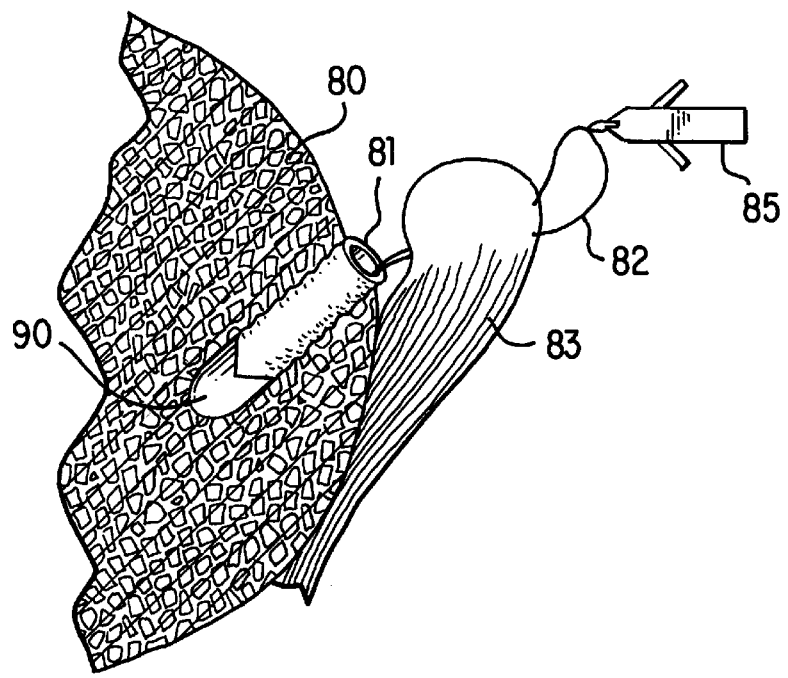

In FIG. 9, the repair continues and the suture loop element 82 is pulled further through tissue 83. An anchor assembly 85 is introduced for the purposes of snagging the suture loop 82. Depicted is anchor assembly of FIG. 1, though any suitable anchor with a snag means or recess can be utilized.

Figure 10:
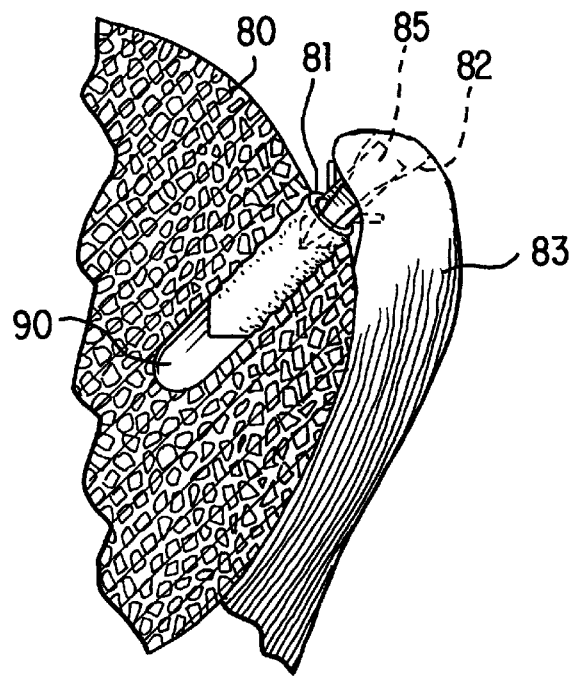

In FIG. 10, the anchor means 85 engages the suture loop element 82, and more particularly, the anchor means 85 snags the suture loop 82 in its snag means. The anchor means 85 is then inserted into the hollow anchoring sleeve 81, beginning the procedure of pulling the tissue 83 into close proximity to the bone mass 80 to facilitate a repair.

Figure 11:
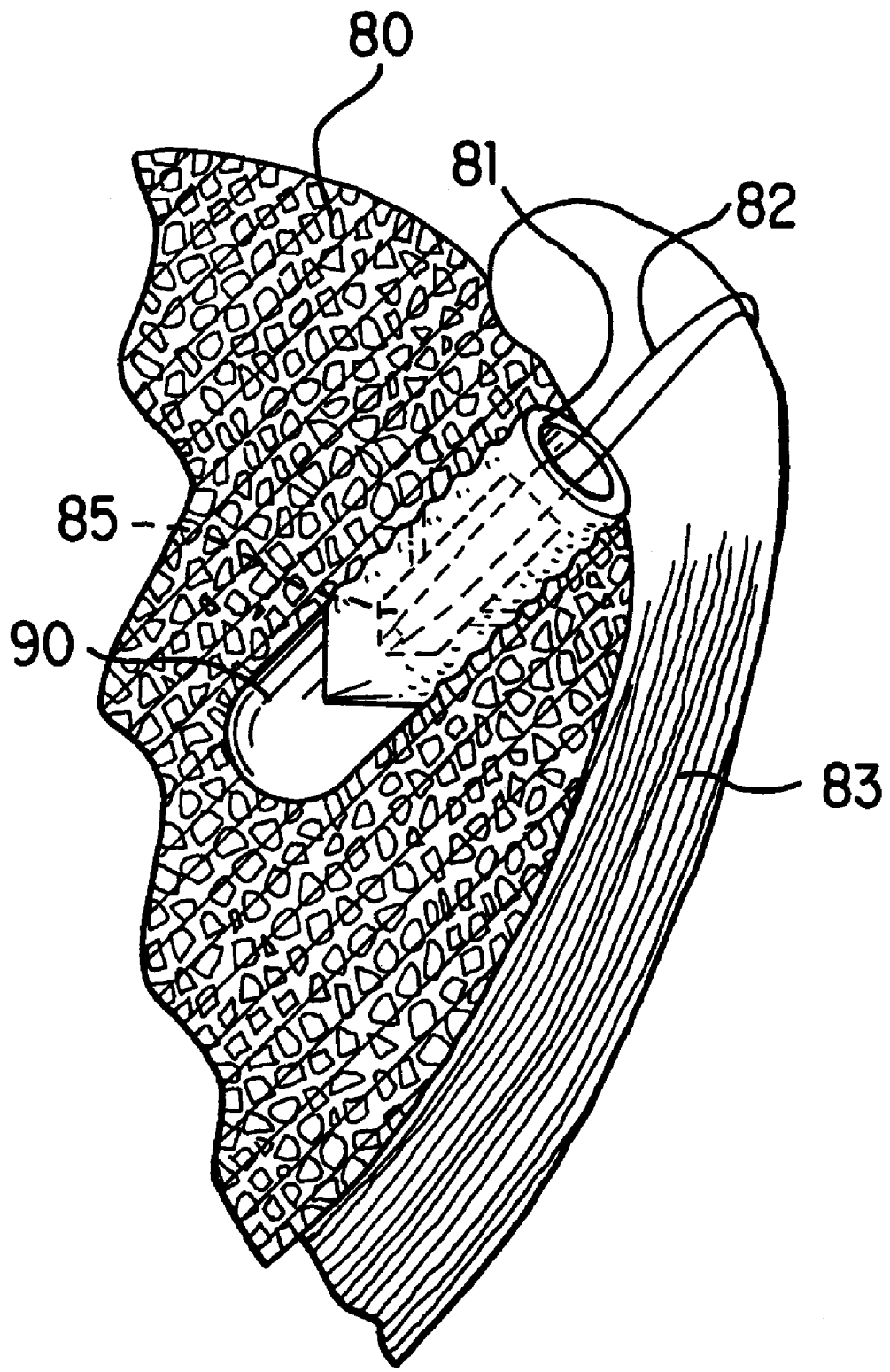

FIG. 11 depicts a completed repair wherein tissue 83 has been attached to bone mass 80 in a secure fashion. The loop section 82 has been captured by anchor means 85 in its snag recess and drawn into the hole 90 in bone mass 80 thereby providing the attachment.

Therefore, there is provided a novel enhanced knotless suture anchor assembly which includes in a preferred embodiment, an anchor means as depicted in FIGS. 1, 2 or 3 and a hollow anchoring sleeve with a suture loop element as depicted in FIGS. 4–7.

In addition to the anchor assembly, there is depicted a method for the attachment of tissue to a bone mass utilizing the novel assembly.

In many situations throughout the discussion above, the terminology "secure attachment of tissue to bone mass" has been used. Such terminology refers to the attachment or reattachment of tissue to a bone mass by securely binding the tissue to the bone mass utilizing the novel loop and sleeve knotless suture anchor assembly. The suture element can be made up of a known suture material, or it can be made of polymer materials, or can be formed of bioabsorbable material such as a polylactide polymer.

While a preferred embodiment of the invention is illustrated, it should be understood that the present disclosure is made by way of example and that variations to the structure shown and its use are possible within the scope of this disclosure without departing from the subject matter coming within the scope of the claims.

What is claimed is:

1. A knotless suture anchor assembly for attachment of tissue to a bone mass, said assembly comprising an anchor means having a snag means located therewith, and a hollow sleeve element with a loop suture element attached thereto, wherein said snag means captures said loop suture element of said hollow sleeve element to draw said tissue into secure attachment with said bone mass.

2. The knotless suture anchor assembly as claimed in claim 1, wherein said snag means is a recess formed in said anchor means to capture said suture loop element of said hollow anchoring sleeve allowing said tissue to be drawn to said bone mass.

3. The knotless suture anchor assembly as claimed in claim 1, wherein said hollow anchoring sleeve has a rough exterior surface for installation and attachment to said bone mass.

4. The knotless suture anchor assembly as claimed in claim 1, wherein said exterior surface has prongs, screws, umbrella spokes for installation and attachment to said bone mass.

5. The knotless suture anchor assembly as claimed in claim 3, wherein said hollow anchoring sleeve has a collar at a top section facilitating its attachment to said bone mass.

6. A method for the attachment of tissue to a bone mass utilizing said knotless suture anchor assembly as claimed in claim 1 comprising the steps of:

a) passing said free standing loop suture element to said tissue; and b) capturing a suture loop element of said hollow anchoring sleeve with said snag means of said anchor means; and installing said anchor means into said hollow anchoring sleeve which is installed in said bone mass for attachment of said tissue to said bone mass.

7. The method for the attachment of tissue to a bone mass utilizing said knotless suture anchor assembly as claimed in claim 1 comprising the steps of:

a) installing said hollow anchoring sleeve into said bone mass;

b) passing said suture loop suture element to said tissue; and c) capturing a suture loop of said hollow anchoring sleeve with said snag means of said anchor means; and installing said anchor means into said hollow anchoring sleeve.

8. The knotless suture anchor assembly as claimed in claim 1, wherein the snag means is an element attached to said anchor means to capture said suture loop element of said hollow anchoring sleeve allowing said tissue to be drawn to said bone mass.

* * * * *